United States Patent [19]

Tedder et al.

[11] Patent Number: 5,316,920
[45] Date of Patent: May 31, 1994

[54] LYMPHOCYTE ACTIVATION ANTIGEN HB15, A MEMBER OF THE IMMUNOGLOBULIN SUPERFAMILY

[75] Inventors: Thomas F. Tedder, South Natick; Liang-Ji Zhou, Boston, both of Mass.

[73] Assignee: Dana-Faber Cancer Institute, Inc., Boston, Mass.

[21] Appl. No.: 870,029

[22] Filed: Apr. 17, 1992

[51] Int. Cl.$^5$ .............. C12N 15/13; C12N 15/14; C12N 5/16
[52] U.S. Cl. .............. 435/69.3; 435/69.7; 435/240.2; 435/320.1; 536/23.5; 536/23.53; 536/24.31; 530/350
[58] Field of Search ............ 536/23.5, 24.3; 435/320.1, 240.2, 69.1, 69.3; 530/350, 395, 388.2

[56] References Cited

PUBLICATIONS

Kozlow, E. J., et al. (1993) Blood 81:454–61.
Wang, P. L., et al. (1992) J. Immunol. 148:2600–08.
Kasinrerk, W., et al. (1992) 1, 149:847–54.
Brunet, J. F., et al. (1988) Immunol. Rev. 103:21–36.
Williams et al., "The Immunoglobulin Superfamily . . . Domains for Cell Surface Recognition," Ann. Rev. Immunol. 6:381–405 (1988).
Littman et al., "The Isolation and Sequence of the Gene Encoding T8: A Molecule Defining Functional Classes of T-Lymphocytes," Cell 40:237–246 (1985).
Johnson et al., "Striking similarities between antigen receptor J pieces and sequence in the second chain of the murine CD8 antigen," Nature 323:74–76 (1986).
Aruffo et al., "Molecular cloning of two CD7 (T-Cell leukemia antigen) cDNAs by a COS cell expression system," EMBO J. 6:3313–3316 (1987).
Williams et al., "Neuronal Cell Thy-1 Glycoprotein: Homology with Immunoglobulin," Science 216:696–703 (1982).
Aruffo et al., "Molecular cloning of a CD28 cDNA by a high-efficiency COS cell expression system," Proc. Natl. Acad. Sci. USA 84:8573–8577 (1987).

Brunet et al., "A new member of the immunoglobulin superfaimly . . . CTLA-4," Nature 328:267–270 (1987).
Lemke et al., "Isolation and Sequence of a cDNA Encoding the Major Structural Protein of Peripheral Myelin," Cell 40:501–508 (1985).
Gold et al., "Isolation of cDNA clones encoding the 20K non-glycosylated polypeptide chain of the human T-cell receptor/T3 complex," Nature 321:431–434 (1986).
van den Elsen et al., "Isolation of cDNA clones encoding the 20K T3 glycoprotein of human T-cell receptor complex," Nature 312:413–418 (1984).
Hermanson et al., "B29: A member of the immunoglobulin gene superfamily exclusively expressed on B-lineage cells," Proc. Natl. Acad. Sci. USA 85:6890–6894 (1988).
Sakaguchi et al., "B lymphocyte lineage-restricted expression of mb-1, a gene with CD3-like structural properties," EBMO J. 7:3457–3464 (1988).
Turka et al., "CD28 is an inducible T-cell surface antigen that transduces a proliferative signal in CD3+ mature thymocytes," J. Immunol. 144:1646–1653 (1990).
Harper et al., "CTLA-4 and CD28 activated lymphocyte molecules are closely related in both mouse and human as to sequence, message expression, gene structure, and chromosomal location," J. Immunol. 147:1037–1044 (1991).

(List continued on next page.)

Primary Examiner—Robert J. Hill, Jr.
Assistant Examiner—David L. Fitzgerald
Attorney, Agent, or Firm—Weingarten, Schurgin, Gagnebin & Hayes

[57] ABSTRACT

Lymphocyte activation antigen HB15, and the human cDNA and gene sequences encoding HB15, are disclosed. HB15 is not expressed at detectable levels by circulating leukocytes but has a unique pattern of expression among tissues. HB15 is uniquely expressed by Langerhans cells within the skin and other subpopulations of dendritic cells. Also disclosed are antibodies reactive with HB15 and methods of using anti-HB15 antibodies, or other antagonists to HB15 function, to treat an immunological disorder, disease or syndrome.

14 Claims, 8 Drawing Sheets

OTHER PUBLICATIONS

Linsley et al., "T-cell antigen CD28 mediates adhesion with B cells by interacting with activation antigen B7/BB-1", Proc. Natl. Acad. Sci. USA 87:5031–5025 (1990).

Freeman et al., "B7, a new member of the Ig superfamily with unique expression on activated and neoplastic B cells", J. Immunol. 143:2714–2722 (1989).

Linsley et al., "CTLA-4 is a second receptor for the B-cell activation antigen B7", J. Exp. Med. 174:561–569 (1991).

Kaufman et al., "Cysteines in the Transmembrane Region of Major Histocompatibility Complex Antigens Are Fatty Acylated via Thioester Bonds", J. Biol. Chem. 259:7230–7238 (1984).

Rose et al., "the presence of cysteine in the cytoplasmic domain of the vesicular stomatitis virus glycoprotein is required for palmitate addition", Proc. Natl. Acad. Sci. USA 81:2050–2054 (1984).

Lemke et al., "Isolation and Analysis of the Gene Encoding Peripheral Myelin Protein Zero", Neuron 1:73–83 (1988).

Littman et al., "Unusual intron in the immunoglobulin domain of the newly isolated murine CD4 (L3T4) gene", Nature 325:453–455 (1987).

Owens et al., "Organization of the neural cell adhesion molecule (N-CAM) gene: alternative exon usage as the basis for different membrane-associated domains", Proc. Natl. Acad. Sci. USA 84:294–298 (1987).

EMBL Database entry EBV, accession No. V01555 et al.; 1983; Epstein-Barr virus genome. *sequence*.

```
                                      M   S   R   G   L   Q   L   L   L   L   S   A   Y   S   L   A
gaattcCGCC                           ATG TCG CGC GGC CTC CAG CTT CTC CTG CTG AGC TGC TAC AGC CTG GCT    61
           1                                                  10
           ↓                                                   +           +   ⓒ                +
 P   A   T   T   P   E   V   K   V   A   S   E   D   V   D   L   P   T   A
CCC GCG ACG ACG CCG GAG GTG AAG GTG GCT TCC GAA GAT GTG GAC TTG CCC TGC ACC GCC                         121
    20                                                        31
                             +                                 +
 P   W   D   P   Q   V   P   Y   T   V   S   W   K   L   L   E   G   G   E
CCC TGG GAT CCG CAG GTT CCC TAC ACG GTC TGG AAG TTA TTG GAG GGT GGT GAA                                 181
         40                                     50            ▲
                                                               +
 E   R   M   E   T   P   Q   E   D   H   L   R   Q   H   Y   H   Q   K   G
GAG AGG ATG GAG ACA CCA CAG GAA GAC CAC CTC AGG CAG CAC TAT CAT CAG AAG GGG                             241
             60                                 70
                             +                     +               +                                N
 Q   N   G   S   F   D   A   P   N   E   R   P   Y   S   L   K   I   R   N   T
CAA AAT GGT TCT TTC GAC GCC CCC AAT GAA AGG CCC TAT TCC CTG AAG ATC CGA AAC ACT                         301
         80                                     90
     S                       +           ⓒ             +
 T   S   N   S   T   Y   R   T   G   T   L   Q   D   P   D   G   Q   R   N
ACC AGC AAC TCG ACA TAC AGG ACT GGA ACT CTG CAG GAC CCG GAT GGG CAG AGA AAC                             361
        100                                    110
 L   S   G   K   V   I   L   R   V   T   L   L   P   A   Q   R   K   E   T
CTA AGT GGC AAG GTG ATC TTG AGA GTG ACA CTG CTG CCT GCA CAG CGT AAA GAA ACT                             421
        120                                    130
                                                                            ⓒ
 F   K   Y   R   A   E   I   V   A   L   I   V   I   F   Y   L   T
TTT AAG TAC AGA GCG GAG ATT GTC GCT CTG ATT TTC TAC TTA ACA                                             481
        140                                    150
                                 ⓒ
 L   I   I   F   T   T   C (AAG) F   A   R   L   Q   S   I   F   P   D   F   S   K
CTC ATC ATT TTC ACT TGT(AAG)TTT GCA CGG CTA CAG AGT ATC TTC CCA GAT TTT TCT AAA                         541
        160            ▲                       170
 A   G   M   E   R   A   F   L   P   V   T   S   P   N   K   H   L   G   L   V
GCT GGC ATG GAA CGA GCT TTT CTC CCA GTT ACC TCC CCA AAT AAG CAT TTA GGG CTA GTG                         601
```

FIG. 2A

```
        180                                186
 T   P   H   K   T   E   L   V   *
ACT CCT CAC AAG ACA GAA CTG GTA TGA GCAGGATTTC TGCAGGTTCT TCTTCCTGAA GCTGAGGCTC    668
AGGGGTGTGC CTGTCTGTTA CACTGGAGGA GAGAAGAATG AGCCTACGCT CCATTTTCTG GAAGATGGCA TCCTGTGAAG    738
TCCTTCACCT CACTGAAAAC ATCTGGAAGG GGATCCCACC TGGGCAGGCC TCGAAAACCA    808
TCACATGACC ACATAGCATG AGGCCACTGC TGCTTCTCCA TGGCCACCTT TTCAGCGATG TATGCAGCTA    878
TCTGGTCAAC CTCCCTGGACA TTTTTCAGT CATATAAAAG CTATGGTGAG ATGCAGCTGG AAAAGGGTCT    948
TGGGAAATAT GAATGCCCCC AGCTGGCCCG TGAGGACTC CTGTCCTCTT CTGCATCTTG   1018
GGGACATCTC TTTGAATTTT CTGTGTTTTG CTGTACCAGC CCAGATGTTT TACGTCTGGG AGAAATTGAC   1088
AGATCAAGCT GTGAGACAGT GGGAAATATT TAGCAAATAA TTTCCTGGTG TGAAGGTCCT GCTATTACTA   1158
AGGAGTAATC TGTGTACAAA GAAATAACAA GTCGATGAAC TATTCCCCAG CAGGTCTTT TCATCTGGGA   1228
AAGACATCCA TAAAGAAGCA ATAAGAAGA GTGCCACATT TATTTTTATA CTTGTCAAAG   1298
AAGGTTTGTG TTTTTCTGCT TTTGAAATCT GTATCTGTAG TGAGATAGCA TTGTGAACTG ACAGGCAGCC   1368
TGGACATAGA GAGGGAGAAG AAGTCAGAGA ATAGAGAGCT CGGCTGGAAA    1438
TGCTGGGCTG ACGGTGCAGT CTGGGTGCTC CCCACTATCT GGGTGCATGA TCTTGAGCAA   1508
GTTCCTTCTG GTGTCTGCTT TCTCCATTGT AAACCACAAG GCTGTTGCAT GGGCTAATGA AGATCATATA   1578
CGTGAAAATT CTTTGAAAAC ATATAAAGCA TCGAAACTCC ATTGAGTCAT TATCCTTGCT   1648
ATGATGATGG TGTTTTGGGG ATGAGAGGGT GCTATCCATT TCTCATGTTT GAAACAAAGA   1718
AGGTTACCAA GAAGCCTTTC CTGTAGCCTT CTGTAGGAAT TCC                                    1761
```

*FIG. 2B*

LYMPHOCYTE ACTIVATION ANTIGEN HB15, A MEMBER OF THE IMMUNOGLOBULIN SUPERFAMILY

Part of the work leading to this invention was made with United States Government funds. Therefore, the U.S. Government has certain rights in this invention.

FIELD OF THE INVENTION

This invention relates to nucleic acid sequences encoding human lymphocyte activation antigens, particularly to sequences encoding lymphocyte activation antigen HB15, and to the proteins and polypeptides encoded by those sequences.

BACKGROUND OF THE INVENTION

Many of the cell-surface molecules which regulate immune responses contain conserved structural features similar to those found in immunoglobulin (Ig). These molecules are encoded by genes that are presumed to have evolved from a common precursor and are therefore members of a large superfamily (Williams et al., Annu. Rev. Immunol 6:381–405 (1988)). Many of the Ig superfamily members are involved in cell-cell adhesion and signal transduction. While most members of this family contain multiple linearly-assembled Ig-like domains, several proteins have been identified that contain single Ig-like domains. Single Ig-like domain proteins that are known or assumed to be involved in cell-cell adhesion include: CD8α (Littman et al., Cell 40:237 (1985)), CD8β (Johnson et al., Nature 323:74 (1986)), CD7 (Aruffo et al., EMBO J. 6:3313 (1987)), Thy-1 (Williams et al., Science 216:696 (1982)), CD28 (Aruffo et al., Proc. Natl. Acad. Sci. USA 84:8573 (1987)), CTLA-4 (Brunet et al., Nature 328:267 (1987)) and Po which is a structural protein of the peripheral myelin sheath (Lemke et al., Cell 40:501 (1985)). In addition, others associate with the antigen receptors of B and T lymphocytes forming multimeric signal-transducing complexes including; CD3 γ, δ and ε chains (Gold et al., Nature 321:431–434 (1986); van den Elsen et al. Nature 312:413–418 (1984)), B29 (Hermanson et al., Proc. Natl. Acad. Sci., USA 85:6890 (1988)), and mB1 (Sakaguchi et al., EMBO J. 7:3457–3464 (1988)).

Two single Ig-like domain containing proteins found on lymphocytes are preferentially associated with cellular activation and are known to be involved in mediating cell-cell interactions. CD28 is expressed much more on activated than nonactivated T and B lymphocytes (Turka et al., J. Immunol. 144:1646 (1990)), and CTLA-4 is expressed mostly, if not exclusively, by activated T and B lymphocytes (Brunet et al., Nature 328:267 (1987); Harper et al., J. Immunol. 147:1037–1044 (1991)). The role of CD28 as a T cell receptor for the B7 molecule expressed by activated B cells has been recently identified (Linsley et al., Proc. Natl. Acad. Sci. USA 87:5031–503 (1990); Freeman et al., J. Immunol. 143:2714–2722 (1989)), as has a similar role for CTLA-4 (Linsley et al., J. Exp. Med. 174:561–569 (1991)). As with CD28 and B7, most of the Ig-like domain-containing receptors interact with other members of the Ig superfamily present on other cells.

SUMMARY OF THE INVENTION cDNAs loned from a human lymphocyte library were analyzed and shown to encode a novel cell-surface glycoprotein, termed HB15, expressed by activated lymphocytes. The mature 186 amino acid protein encoded by the CDNA was composed of a single extracellular V type immunoglobulin (Ig)-like domain, a transmembrane domain and a 39 amino acid cytoplasmic domain. Northern blot analysis revealed that HB15 derives from three MRNA transcripts of ~1.7, 2.0 and 2.5 kb expressed by lymphoblastoid cell lines. Monoclonal antibodies reactive with HB15 were produced and used to show that HB15 is expressed as a single chain cell-surface glycoprotein of $M_r$ 45,000. HB15 expression was specific for lymphoblastoid cell lines and mitogen-activated lymphocytes; HB15 was not expressed at detectable levels by circulating leukocytes. Immunohistological analysis revealed that HB15 has a unique pattern of expression among tissues, being found predominantly in hematopoietic tissues with scattered expression by interfollicular cells and weak expression by mantle zone and germinal center cells. Uniquely, HB15 is also expressed by Langerhans cells within the skin and circulating dendritic cells. Thus, the HB15 glycoprotein represents a new member of the Ig superfamily.

cDNA sequences encoding the HB15 protein or portions thereof, including any of its specific domains, ligand binding fragments or immunospecific fragments, can be incorporated into replicable expression vectors and the vectors transfected into an appropriate host (e.g., a bacterial, yeast, or eucaryotic cell culture). Alternatively, genomic DNA fragments encoding the HB15 protein or portions thereof can be utilized in situ. The expressed proteins or polypeptides, or antagonists thereto, can be used to modulate mammalian immune function. Also, the expressed products can be employed as immunogens in order to raise antibodies against HB15 or portions thereof including any of its specific domains or fragments thereof.

Thus, the invention generally features nucleic acid isolates encoding lymphocyte activation antigen, HB15, or portions thereof including any of its specific domains, ligand binding fragments or immunospecific fragments; the encoded HB15 protein or portions thereof including specific domains, ligand binding fragments and immunospecific fragments; methods of producing HB15 or portions thereof; methods of detecting the presence of HB15 or of an HB15 ligand; methods of identifying or developing antagonists to HB15 or HB15 ligand function; methods of diagnosing or treating a patient suffering from an immunological disorder, methods of identifying or of isolating cells that express HB15 or fragments thereof, and antibodies reactive with HB15 or fragments thereof.

Also featured are derivatives of HB15 having variant amino acid sequences or glycosylation not otherwise found in nature, the nucleic acid isolates encoding such derivatives, and polynucleotide probes capable of hybridizing under stringent conditions to the HB15 gene.

As used herein the term "antagonist to HB15" includes any agent which interacts with HB15 and interferes with its function, e.g., antibody reactive with HB15 or any ligand which binds to HB15. The term "identify" is intended to include other activities that require identification of an entity, such as isolation or purification. The terms "isolated" or "essentially purified" refer to a nucleic acid or protein sequence that has been separated or isolated from the environment in which it was prepared or in which it naturally occurs. Such nucleic acid or protein sequences may be in the form of chimeric hybrids, useful for combining the function of the nucleic acid or protein sequences of the invention with other species. The term "immunospecific fragment" refers to a fragment of the indicated protein that reacts with antibodies specific for a determinant of the indicated protein.

The HB15 protein, immunospecific or ligand binding fragments or specific domains thereof, or other antagonists to HB15 that interfere with HB15 function, can be used therapeutically to modify or inhibit the development or progression of an immune response or cellular interaction, or to deliver drugs, toxins, or imaging agents to cells that express HB15. HB15 CDNA can be used to produce these proteins or peptide fragments; to identify nucleic acid molecules encoding related proteins or polypeptides (e.g., homologous polypeptides from related animal species and heterologous molecules from the same species); or to build other new, chimeric molecules having similar function either in transformed cells or in cell free systems. In addition, HB15 CDNA can be used to synthesize antisense oligonucleotides for inhibiting the expression of the HB15 protein. Thus, the invention also encompasses a nucleic acid sequence greater than about 10 bp, capable of hybridizing under stringent conditions to the complement of the nucleic acid sequence encoding HB15 and shown in FIG. 2. This nucleic acid sequence may also be greater than 20 bp, 50 bp or 100 bp. production or expression by cells are made possible by the development of monoclonal antibodies selectively reactive with the HB15 protein.

Other features and advantages of the invention will be apparent from the following description of the preferred embodiments thereof and from the claims.

BRIEF DESCRIPTION OF THE DRAWINGS

FIGS. 2A and 2B shows the cDNA nucleotide sequence and the deduced amino acid sequence (described herein as SEQ ID NO: 1) of HB15; the vertical arrow represents the predicted cleavage site for generation of the mature protein; numbers shown above the amino acid sequence designate amino acid residue positions of the putative mature protein; numbers to the right of the nucleotide sequence designate nucleotide positions; the * indicates the translation termination codon; underlined nucelotides delineate translated regions with hydrophobic character; underlined amino acids indicate potential N-linked glycosylation attachment sites; wavy underlining delineates a poly(A) attachment signal sequence; amino acids conserved in Ig-like domains are indicated by (+); cysteine residues are circled; arrow heads below the nucleotide sequence denote exon/intron boundaries;

DESCRIPTION OF THE PREFERRED EMBODIMENTS

Figure 1:
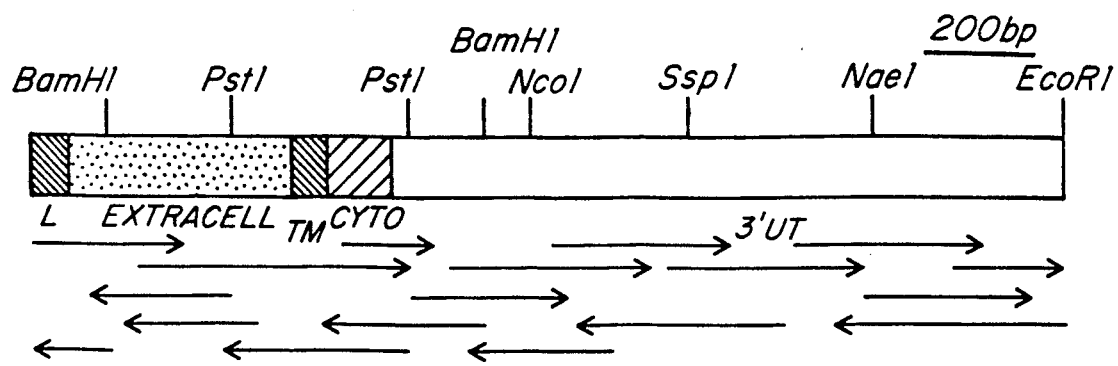
FIG. 1 shows the structure of the HB15 CDNA clone and the location of restriction sites, showing the extracellular domain ("extracell"), the transmission domain ("TM"), and the 3' untranslated region (3'UT)

The lymphocyte activation antigen, HB15 expressed exclusively by lymphoid tissue and Langerhans skin cells. Referring to FIG. 1, the structural features of the HB15 protein, predicted from nucleotide sequence derived from multiple CDNA clones, clearly establish it as a new member of the Ig superfamily. The predicted structure of HB15 is that of a typical membrane glycoprotein with a single extracellular Ig-like domain, a transmembrane domain and an approximately 40 amino acid cytoplasmic domain. It is likely that the entire coding region for HB15 was identified as transfection of cell lines with the pHB15 CDNA generated cell surface expression of the protein and the $M_r$ of the immunoprecipitated protein was similar in both CDNA transfected cells (~45,000) and HB15+ Raji cells (~40,000). It is also likely that HB15 undergoes extensive post-translational processing as HB15 was expressed as a single chain molecule, yet the determined $M_r$ was twice the predicted size of the core protein. Since HB15 was also expressed on the surface of CDNA transfected cells, including COS cells, CHO cells, a mouse pre-B cell line and a human erythroleukemia line, it is likely that surface expression is not dependent on expression of other components of a molecular complex as occurs with the Ig-like proteins that associate with the T and B cell antigen receptors.

Comparison of the HB15 amino acid sequence (SEW ID NO: 2) with other previously identified proteins did not reveal any striking homologies, except the similarity of the extracellular Ig-like domain with other members of the Ig superfamily. The HB15 Ig-like domain contained many of the conserved features found in the V-set of domains as shown in FIG. 2 (Williams et al., Ann. Rev. Immunol. 6:381–405 (1988) Based on the homology with Ig domains, HB15 is likely to possess a disulfide bond linking Cys 16 and Cys 88. This would place 71 amino acids between the two Cys residues which is of the appropriate size for V-related domains (Williams et al., supra) . There is the potential for additional disulfide bond formation between residues at positions 8, 81 and 110 since these Cys are present in the extracellular domain as well. In addition, HB15 has a Cys residue located within the predicted membrane spanning domain at position 144. Cys residues are also located at identical positions in CD3δ and CD7, suggesting some functional significance, perhaps as sites for fatty acylation (Kaufman et al. , J. Biol. Chem. 259:7230–7238, (1984) ; Rose et al. , Proc. Natl. Acad. Sci. , USA 81:2050–2054 (1984) ) . The HB15 cytoplasmic tail is similar in size to that of CD7 (Aruffo et al., EMBO J. 6:3313 (1987)), but shared no amino acid sequence similarity with known proteins. However, the five Ser/Thr residues within this domain could serve as potential sites of phosphorylation. Thus, HB15 appears to be a newly described lymphocyte cell surface antigen that shares no apparent relatedness with previously described structures.

The HB15 extracellular domain is different from the typical Ig-like domain in that it is encoded by at least two exons. Analysis of partial genomic DNA sequence revealed that half of the Ig-like domain is encoded by a single exon and the putative membrane spanning domain is also encoded by a distinct exon (FIG. 2). That Ig-like domains can be encoded by more than one exon has been observed for some members of the Ig superfamily, including the Po protein (Lemke et al., Neuron 1: 73–83 (1988) CD4 (Littman et al., Nature 325:453–455 (1987)) and N-CAM (Owens et al., Proc. Natl. Acad. Sci., USA 84:294–298 (1987)). This finding supports structural analyses which suggested that Ig domains may have arisen from an ancestral half-domain that evolved through duplication and subsequent adjoining. However, each of the above genes and the HB15 gene contain introns at different locations between the sequences coding for the conserved Cys residues of the disulfide bond (Williams et al., Annu. Rev. Immunol. 6:381–405 (1988)). This finding supports the notion that introns may have been subsequently inserted to interrupt the ancestral Ig-like domain at later points during the evolution of each of these domains.

Expression of HB15 appears to be generally restricted to lymphocytes since two monoclonal antibodies reactive with HB15 failed to detect HB15 on most other hematopoietic cells. HB15 expression may be a late event in lymphocyte development as most thymocytes and circulating lymphocytes did not express detectable levels of cell surface HB15. However, after being activated by mitogens, peripheral lymphocytes expressed maximal levels of cell surface HB15 on days 3 through 5, the period of time during which maximal proliferation occurred. HB15 may be expressed at low levels by monocytes, especially after culture or activation, but the level of expression is low and may just result from Fc receptor mediated antibody attachment. Many T and B cell lines also expressed HB15, but expression was generally at low levels. Interestingly, cell-surface HB15 expression by cell lines was highest during periods of maximal proliferation such as on the first day after the cultures were fed. These results imply that HB15 is important for maximal growth of lymphoblastoid cells or the maximal growth of cells is critical for the expression of this antigen. This was consistent with the observation that HB15 was expressed by germinal center cells in hematopoietic tissues. Nevertheless, HB15 expression appeared to be lymphoid tissue restricted as revealed by immunohistological analysis of twenty-two different tissues. The only exception was the finding that skin Langerhans cells express HB15. This unique pattern of restricted expression, along with the structural analysis of the protein, indicates that HB15 is a newly identified lymphocyte activation antigen.

The structural similarity of HB15 with other members of the Ig superfamily suggests that it may be involved in cellular interactions since Ig-like domains are frequently involved in a variety of homotypic and heterotypic interactions in the immune and nervous systems. These interactions include binding functions that trigger a subsequent event below the cell surface or adhesion. A key functional feature is that homophilic or heterophilic binding usually occurs between Ig-related molecules, and this is often between molecules on opposed membrane surfaces. The structural relatedness of HB15 to these other proteins may imply a role for this lymphocyte activation protein in either homotypic or heterotypic interactions of lymphocytes following activation or other HB15+ cell types.

It is understood that the particular nucleotide and amino acid sequences disclosed in FIG. 2 (SEQ ID NO: 1 and SEQ ID NO: 2) are representative of the counterpart and related human genes and proteins that can conveniently and directly be obtained following the teaching of this disclosure. For example, cross-hybridization under stringent conditions of the disclosed nucleic acid sequences with genetic material from human cells, can readily be performed to obtain equivalent human sequences. In an analogous manner, degenerate oligonucleotides can readily be synthesized from the disclosed amino acid sequence, or portions thereof, and amplified using any well-known amplification technique, such as the polymerase chain reaction, to obtain probes that bind to equivalent human sequences. Proteins or polypeptides encoded by equivalent sequences can be produced. Antibodies directed against the disclosed protein or peptides can also be raised and employed to cross-react with human and other mammalian peptides having similar epitope(s). Those peptides isolated in this manner that have similar antibody reactivity patterns to those of the disclosed proteins or peptides are considered equivalents of the disclosed proteins or peptides.

The following examples are presented to illustrate the advantages of the present invention and to assist one of ordinary skill in making and using the same. These examples are not intended in any way otherwise to limit the scope of the disclosure.

EXAMPLE I

Isolation and characterization of HB15 CDNA clones and characterization of the HB15 protein A human tonsil CDNA library was screened by differential hybridization using labeled CDNA from the B lymphoblastoid cell line Raji and the T cell line H-SB2. Two of the 261 RAJI+ H-SB2− CDNA clones isolated, pB10 (~2.5 kb) and pB123 (~1.2 kb), cross hybridized, yet failed to hybridize with cDNAs that encode known B cell surface antigens (Tedder et al., Proc. Natl. Acad. Sci., USA 85:208 (1988)). Expression of this MRNA was examined by Northern blot analysis using poly(A)+ RNA isolated from B cell lines (NALM-6, Namalwa, Daudi, SB, and Raji), T cell lines (Hut-78, H-SB2, and MOLT-3) and the erythroleukemia line, K562. The pB123 CDNA hybridized strongly with three MRNA species of ~1.7, ~2.0 and ~2.5 kb in SB and Raji. Daudi and Namalwa cells expressed lower levels of this MRNA. Further autoradiography of the blot (7 days) revealed that the NALM-6, Hut-78 and MOLT-3 cells also expressed these three MRNA species, but at much lower levels, and faint hybridization with H-SB2 RNA was detected. These results suggested differential expression of this gene among leukocyte subpopulations.

Restriction maps were generated for these cDNAs and their nucleotide sequences determined. Both cDNAs were overlapping and contained open reading frames at their 5' ends with the pB123 cDNA having the longest 5' sequence. Since neither clone contained a translation initiation site, the pB10 CDNA insert was used to isolate 13 additional cross-hybridizing CDNA from a human tonsil library. Restriction maps and nucleotide sequence determination indicated that 12 of the cDNAs were overlapping, with one CDNA having the longest sequence at the 5' end. The restriction map and nucleotide sequence of this clone, termed pHB15, are shown in FIG. 1 and FIG. 2, respectively. The full length cDNA clone is likely to include an ~500 bp fragment at the 3' end that was removed from the cDNA by EcoR I digestion and subcloning. Eight other independent cDNA clones had similar EcoR I generated fragments and an EcoR I site was located at the identical nucleotide position in all cDNAs that were sequenced.

The pHB15 cDNA had a 625 bp open reading frame, with the major portion of the cDNA representing untranslated sequence. The determined nucleotide sequence and predicted amino acid sequence of HB15 are given in FIG. 2 and described herein as SEQ ID NO: 1 and SEQ ID NO: 2. The predicted cleavage site used to generate the mature protein is shown by a vertical arrow. The numbers shown above the amino acid sequence designate amino acid residue positions of the putative mature protein and the numbers on the right designate nucleotide positions. Amino acids are designated by the single-letter code, and * indicates the termination codon. Nucleotides delineating translated regions with hydrophobic character are underlined. Amino acids indicating potential N-linked glycosylation attachment sites are underlined. A poly(A) attachment signal sequence is indicated by wavy underlining. The Cys residues are circled and amino acids which are often conserved in Ig-like domains are indicated by (+). Arrow heads below the nucleotide sequence denote exon/intron boundaries identified in another DNA clone.

The first ATG shown is the most likely initiation codon for translation since it conforms to the proposed translation initiation consensus sequence, (A/G)-CCAUG (Kozak, Cell 44:283-292 (1986)). It is likely that the different MRNA species result from differential use of poly(A) attachment sites, AATAAA, since one was found at nucleotide position 1248 in the middle of the 3' untranslated region (FIG. 2). This poly(A) attachment site was functional in the pB123 cDNA since it was followed by a poly(A) tail. A poly(A) attachment site or tail was not found in the ~550 bp EcoR I fragment which presumably represents the 3' end of the pHB15 cDNA.

One clone isolated from the cDNA library (~3.0 kb long) that hybridized with the pB123 cDNA had a unique sequence with 229 and 107 bp long segments that were identical to those found in the other cDNAs. These regions had flanking sequences that corresponded to the consensus 5' and 3' splice sequences which demark exon boundaries (Aebi et al., Trends Genet. 3:102-107 (1987)) indicating that this aberrant cDNA was composed of introns and two exons. The three splice junction sites identified by this clone are shown (FIG. 2).

The predicted length of the HB15 protein was 205 amino acids (FIG. 2). However, the pB123 cDNA was missing the codon AAG at nucleotide position 500 so the protein may be one amino acid shorter in some cases. This may result from differential splicing at an exon/intron border, that results in the inclusion or loss of a codon since this codon abuts a potential splice site. A similar phenomenon has been found in the CD19 gene which also encodes a member of the Ig superfamily (Zhou et al., Immunogenetics 35:102-111 (1992)). Hydropathy analysis of the HB15 amino acid sequence by the method of Kyte et al., J. Mol. Biol. 157:105 (1982) revealed two regions of strong hydrophobicity. The first hydrophobic stretch of 19 amino acids represents a typical signal peptide at the amino terminal end of the protein. The algorithm of von Heijne, Nucleic Acids Res. 14:4683-4690 (1986) predicts that the most probable amino-terminus of the mature protein would be the Thr following amino acid 19. The second hydrophobic region of 22 amino acids most probably represents the transmembrane region. Three potential N-linked glycosylation attachment sites (N-X-S/T) were found in the extracellular domain. Therefore, the predicted molecular mass of the core protein would be ~20,500.

Six Cys residues were found in the extracellular domain of HB15 and one in the putative membrane spanning domain. One pair of these residues at positions 16 and 88 delineate Ig-like domains (Williams et al., Annu. Rev. Immunol. 6:381-405 (1988)). This domain contained many of the hallmark amino acids which define the V set of Ig-like domains. A computer search of protein sequences using the Protein Identification Resource Protein Sequence Database showed that no proteins shared significant sequence homology with HB15 other than some members of the Ig superfamily.

Figure 3:
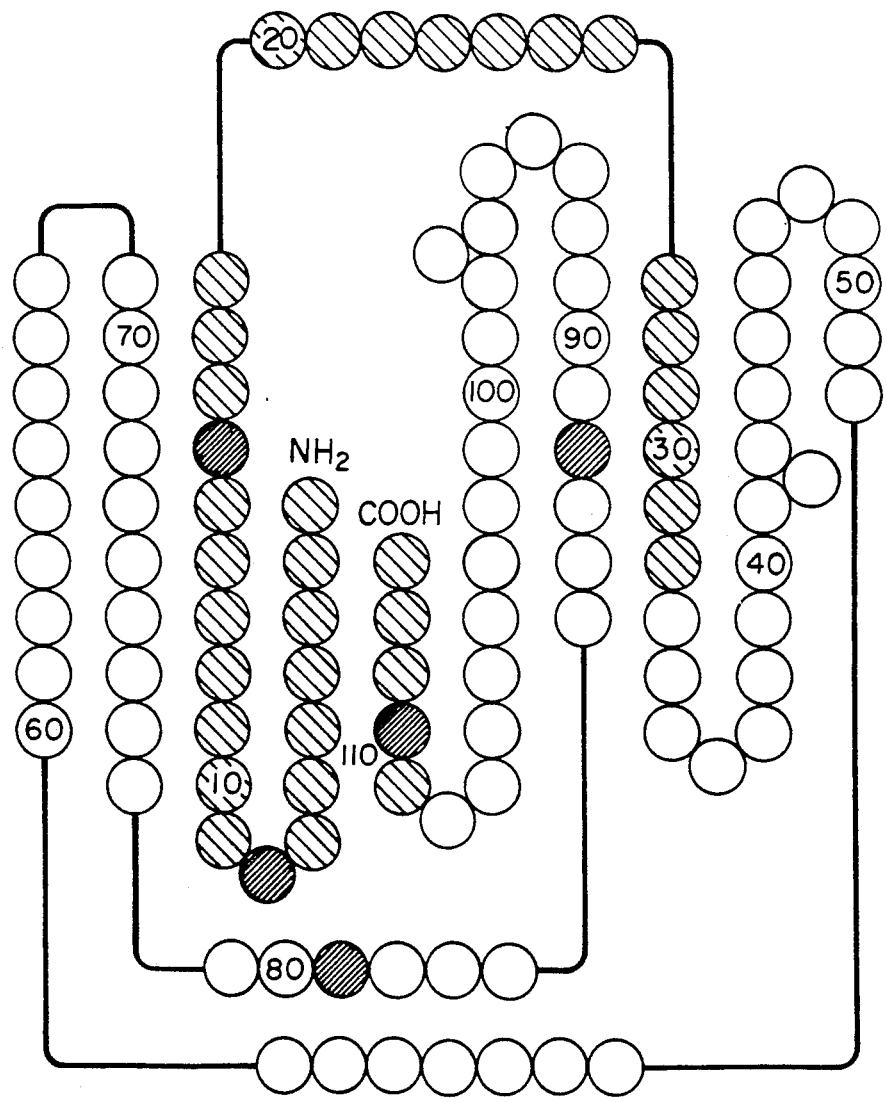
FIG. 3 shows a hypothetical model for the structure of the extracellular domain of HB15 cystein residues are shown as filled in circles; amino acids encoded by different exons are indicated by alternatively shaded circles; numbers represent the predicted amino acid residue positions as shown in FIG. 2.

Referring to FIG. 3, a hypothetical model is given for the structure of the extracellular domain of HB15 based on the proposed arrangement of the β-pleated sheets for the V domain of Ig heavy chain. cys residues are represented as filled circles and amino acids encoded by different exons are indicated by alternatively shaded circles. Numbers represent the predicted amino acid residue positions as in FIG. 2.

EXAMPLE II

Production of monoclonal antibodies reactive with HB15.

Hybridomas were generated by the fusion of NS-1 myeloma cells with spleen cells obtained from mice immunized with pHB15 cDNA-transfected COS cells. Monoclonal antibodies reactive in indirect immunofluorescence assays with HB15 MRNA positive cell lines, but not with HB15 negative cell lines, were isolated. Two of these antibodies, anti-HB15a (IgG$_{2b}$) and anti-HB15b (IgG$_3$) also reacted with COS cells transfected with the pHB15 CDNA, but did not react with cells transfected with CD19 CDNA (Tedder et al., J. Immunol. 143:712-717 (1989)) or the expression vector alone. In addition, these antibodies reacted with a human erythroleukemia cell line, K562, and a mouse pre-B cell line, 300.19, stably transfected with the pHB15 CDNA. The antibodies did not react with untransfected parent cells, cells transfected with vector alone; or CD19, CD20 (Tedder et al., Proc. Natl. Acad. Sci., USA 85:208 (1988)) or LAM-1 (Tedder et al., J. Exp. Med. 170:123-133 (1989)) CDNA transfected cells. In all cases, the reactivities of the anti-HB15a and anti-HB15b mAb were identical.

EXAMPLE III

Detection of HB15 expression

Immunoprecipitation of cell surface HB15

The anti-HB15a mAb was purified, coupled to beads and used to immunoprecipitate HB15 from detergent solubilized extracts of surface-iodinated cell lines. Optimum results were obtained using the K562-HB15 cell line (K562 cells transfected with pHB15 CDNA) since the level of HB15 expression was higher than in other cell lines. The anti-HB15a mAb specifically immunoprecipitated proteins that migrated as a single broad band of ~45,000 $M_r$. Similar results were obtained when the immunoprecipitated materials were run under reducing or nonreducing conditions. A similar protein was immunoprecipitated from the Raji cell line except the $M_r$ was ~40,000. Thus, HB15 was expressed as a noncovalently-associated single chain molecule on the cell surface.

HB15 was expressed by activated lymphocytes.

Figure 4A:
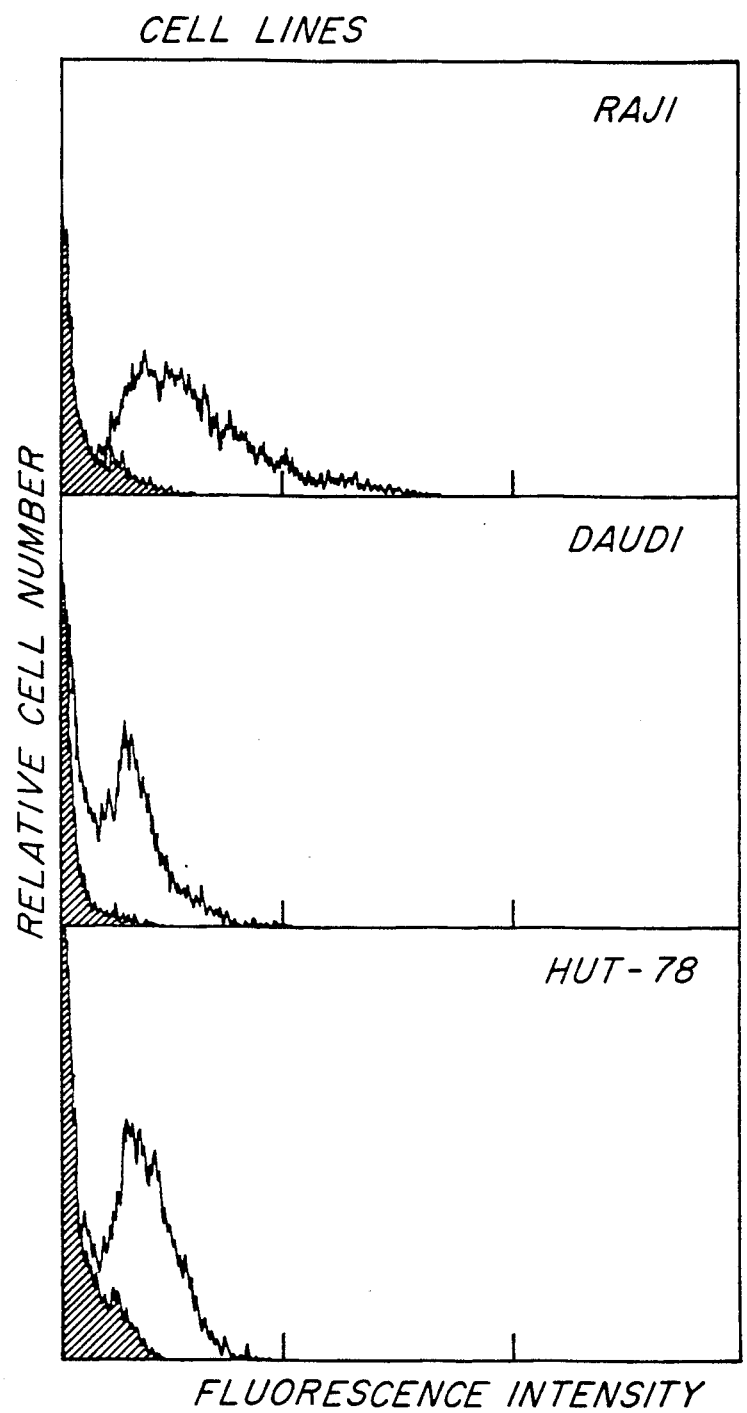
FIGS. 4A and 4B show the immunofluorescence result s obtained with three lymphoblastoid cell lines that express HB15 (A) and with blood lymphocytes before and after mitogen activation (B); open histograms show cellular reactivity with the HB15a antibody; shaded histograms represent background levels of immunofluorescence staining obtained with unreactive control antibodies.
Figure 4B:
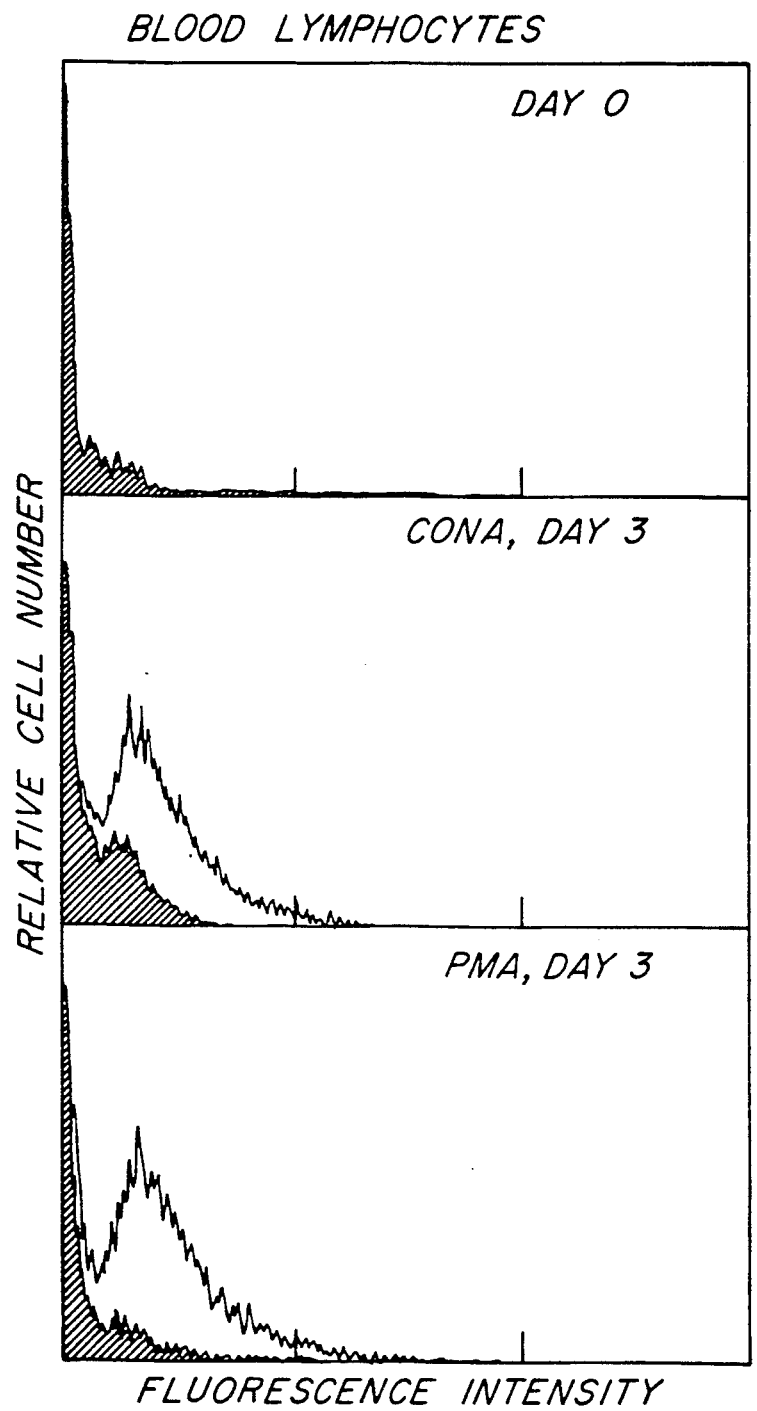

The tissue distribution of the HB15 surface antigen was examined by indirect immunofluorescence staining with flow cytometry analysis. Two cell lines that did not express HB15 message were transfected with the pHB15 CDNA subcloned into the Bam HI site of the retroviral vector PZIPNEDSV(X). Referring to FIG. 4, the immunofluorescence results obtained with three lymphoblastoid cell lines that express HB15 are demonstrated. The open histograms show the cellular reactivity with the HB15a antibody, and the shaded histograms demonstrate background levels of immunofluorescence staining obtained with unreactive control antibodies. Among 33 cell lines examined, HB15 was expressed at detectable levels by B cell lines (including Raji, Daudi, Namalwa, Arent, BJAB, SB, Jijoy, Akata, and SLA) and T cell lines (including Jurkat, H-9, Rex, H-SB2, and Hut-78). However, HB15 expression was generally low and variable. The highest levels of cell-surface expression were always obtained where the cell cultures were recently split and were thus proliferating maximally. Cell lines that did not express detectable levels of HB-15 included: K562; the B cell lines NAI.M-6 and Ramos; the T cell lines, MOLT-3, RPMI 8405, PEER, MOLT-14, CEM and HPB-ALL; the myelomonocytic line, HL60; the natural killer cell line, YT; the colon carcinoma lines, Colo-205 and HT29; the lung cell lines, NCI-H69, and NCI-H82, the prostate line, PC3; the melanoma line, MEWO; and the breast tumor lines, ZRT5.1, MCF7 and BT20.

Expression of HB15 by normal blood leukocytes was also examined. However, cell-surface expression of HB15 was not detected at significant levels on circulating lymphocytes, natural killer cells or monocytes in 15 blood samples. Therefore, the possibility that HB15 was expressed following cellular activation was examined by inducing T lymphocyte proliferation with the mitogens concanavalin A (ConA), pokeweed mitogen, phytohemag-glutinin-P or phorbol esters (PMA). Expression of HB15 was examined 2, 8, 12, 24, 48, 72, 120 and 240 hours following the initiation of cultures. Appearance of HB15 expression paralleled cellular proliferation such that optimal expression was on days 3 through 5 following the initiation of cultures. Also, the quantity of HB15 expression induced was not correlated with any specific mitogen, but correlated more with the strength of the mitogenic signal such that cell-surf ace expression was predominantly found on the larger blast cells. Therefore, HB15 was expressed by lymphocytes following activation.

Immunohistological analysis of HB15 expression

Figure 5A:
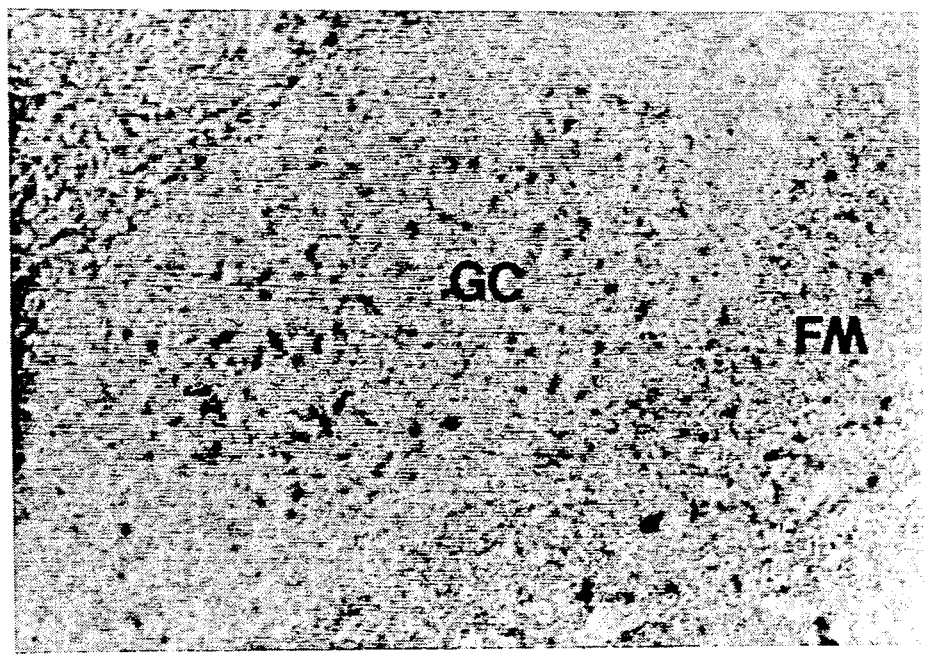
FIGS. 5A–5F show immunohistochemical analysis of HB15 expression in tonsil and lymph node cells (A); germinal centers (B), follicular regions (C), a subpopulation of dendritic cells (D), a subpopulation of medullary cells (E), a subpopulation of dendritic cells (F).
Figure 5B:
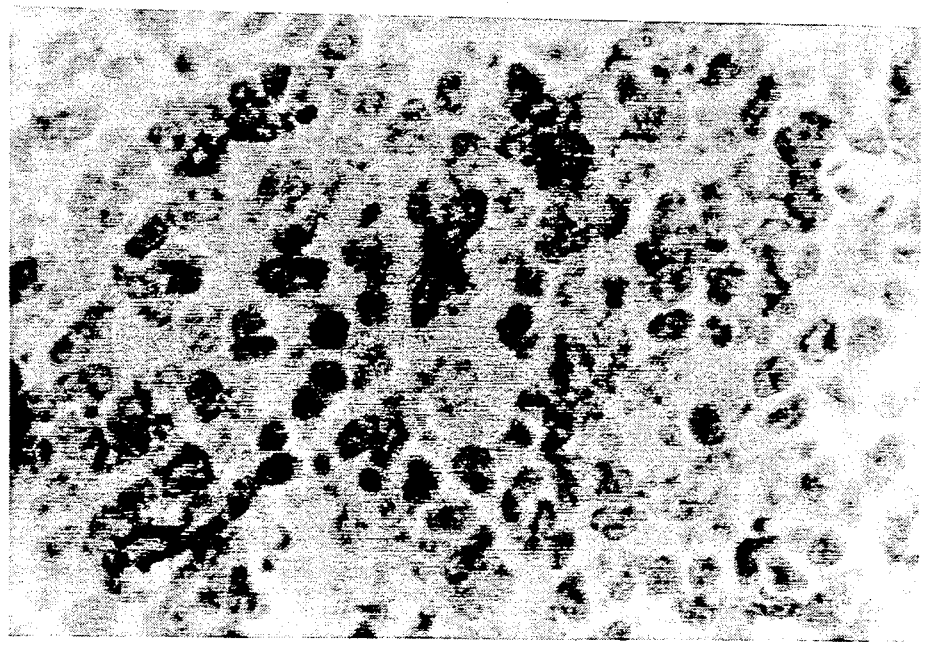
Figure 5C:
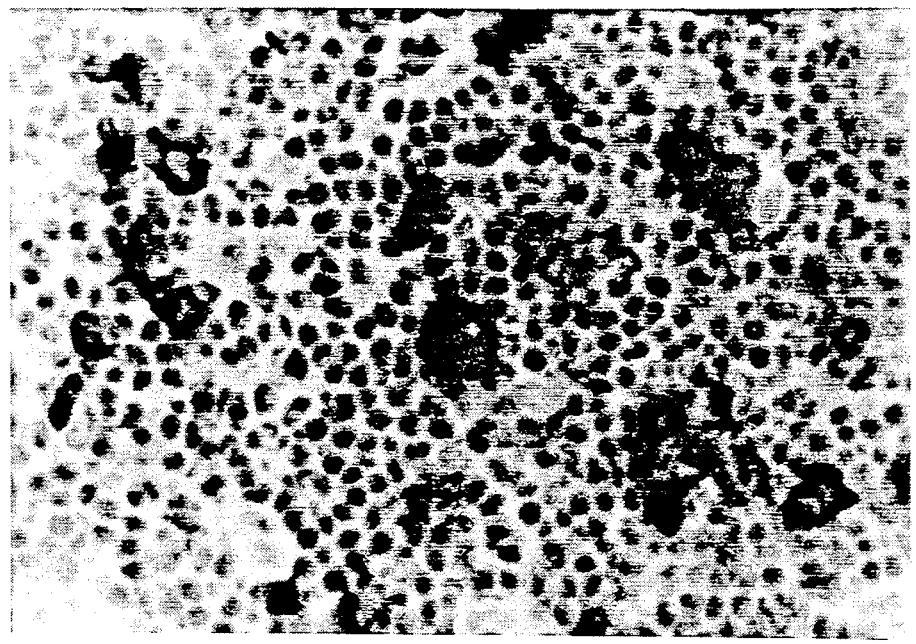
Figure 5D:
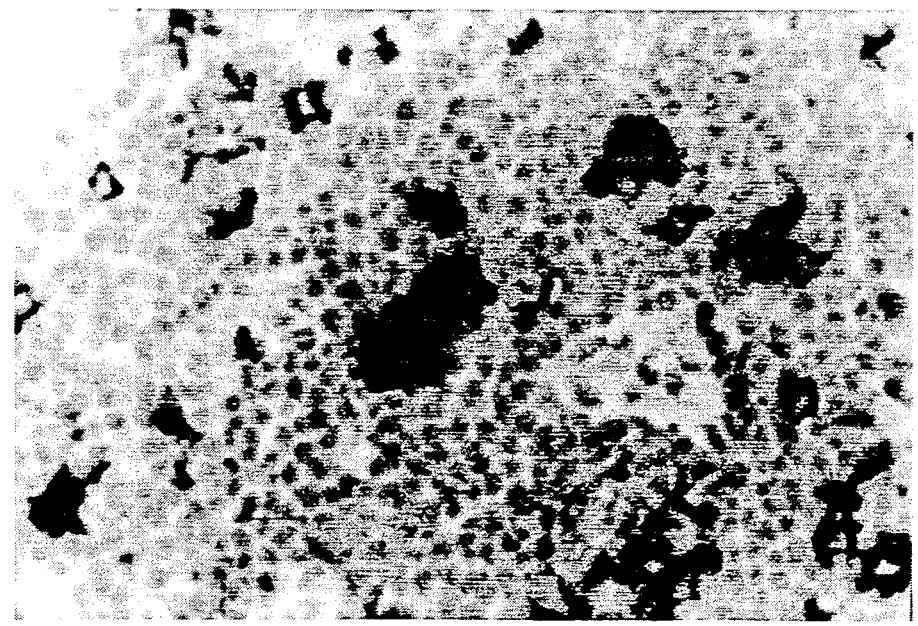
Figure 5E:
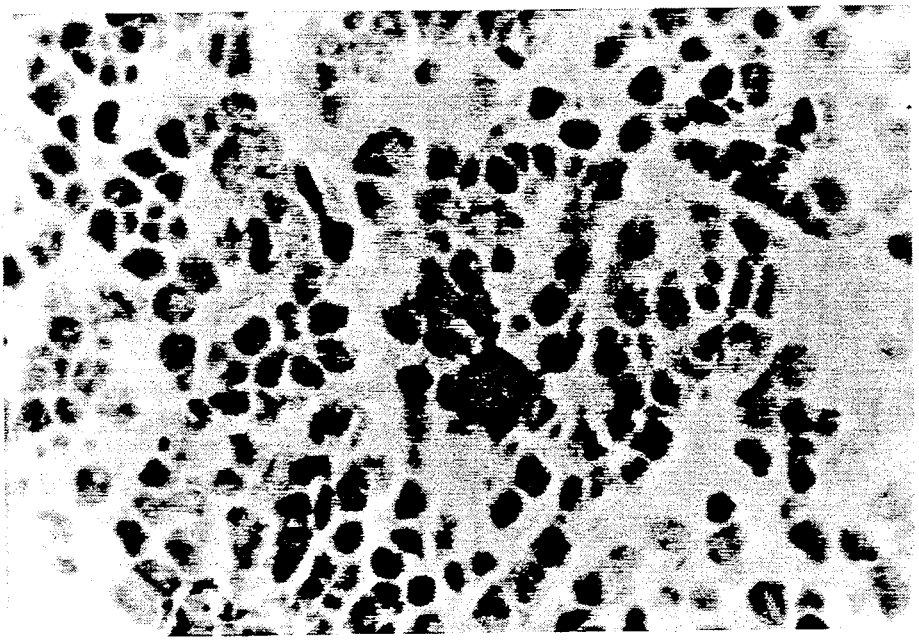
Figure 5F:
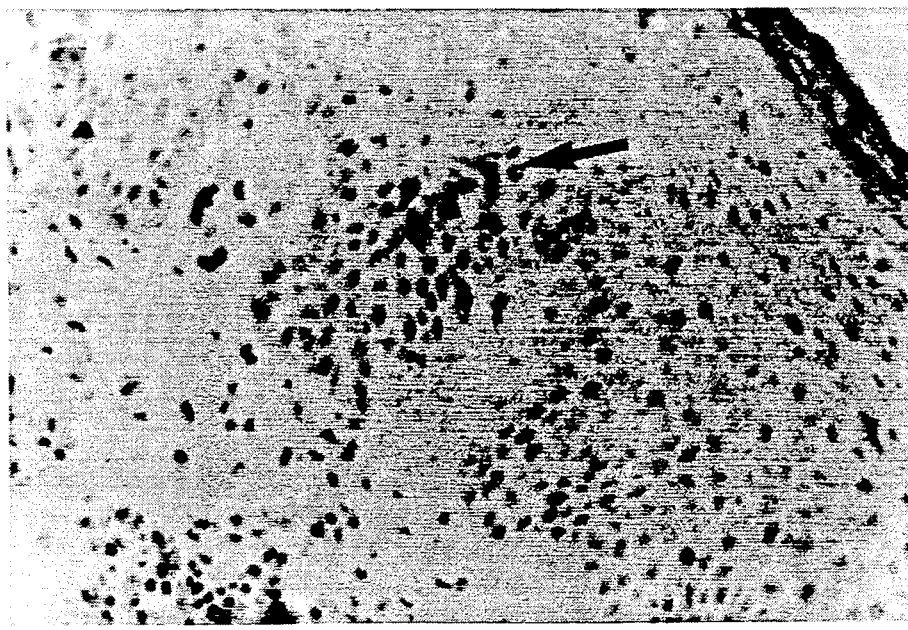

The lymphocyte specificity and tissue distribution of HB15 was also examined by immunohistological analysis of different human tissues. Basically, the anti-HB15a mAb was used to stain thymus, tonsil, spleen, lymph node, kidney, renal pelvis and ureter, Fallopian tube, liver, pancreas, stomach, breast, lung, esophagus, skeletal muscle, skin, uterus, salivary gland, thyroid gland, adrenal gland, heart, appendix and colon. (Referring to FIGS. 5A-5F), in most cases, HB15 expression appeared lymphocyte specific in that no significant reactivity was observed in non-lymphoid tissues. Among tonsil and lymph nodes (FIG. 5A), HB15 was expressed reasonably strongly by scattered cells in intrafollicular regions (T cell zones) (FIG. 5C). Although some of these cells may have been lymphoblasts, most were interdigitating reticulum cells (a subpopulation of dendritic cells) since they appeared larger than resting lymphocytes and expressed the CD1 surface molecule (FIG. 5D). Also, some cells (50-80%) within germinal centers (GC; FIGS. 5A and 5B) and follicular mantle zones (FM; FIG. 5A), with the morphology of lymphocytes, were weakly HB15+. Among spleen, the HB15+ cells were predominantly restricted to the white pulp, whereas the red pulp remained largely negative. Again, these large, scattered positive cells in the white pulp are likely to be interdigitating reticulum cells or lymphoblasts. Cortical thymocytes were HB15 negative, while a small subpopulation of medullary cells, presumably thymocytes, was positive (FIG. 5E). Unlike other non-hematopoietic tissues, analysis of skin revealed that some cells with the characteristic scattered branching morphology of Langerhans cells (a subpopulation of dendritic cells) expressed HB15 at detectable levels (FIG. 5F). Among all non-hematopoietic tissues, where inflammatory infiltrations were apparent, a few scattered lymphocytes were found to express HB15. It is also likely that circulating dendritic cells are HB15+, but because of their low frequency they were not readily detected. Similarly, it is also likely that the malignant counterparts of dendritic cells express HB15 and that this molecule can be used as a diagnostic marker for malignant cells as the L428 cell line, which is a neoplastic cell line that was derived from Hodgkin's disease and may represent interdigitating reticulum cells (Schaadt et al., Int. J. Cancer 26:723-731 (1980)), is HB15 positive.

Experimental Procedures

Isolation of CDNA clones

The isolation of CDNA clones by differential hybridization has been described (Tedder et al., Mol. Immunol. 25:1321-1330 (1988)). One clone, pB123, was purified, labeled by nick translation (Rigby et al., J. Mol. Biol. 113:237-251 (1977)) and used to isolate homologous CDNA by again screening the same human tonsil CDNA library in λgt11 (Weis et al., Proc. Natl. Acad. Sci., USA 83:5639-5643 (1986)) as described (Zhou et al., Immunogenetics 35:102-111 (1992)). Positive plaques were isolated, cloned and the CDNA inserts were removed by EcoR I digestion and subcloned into pSP65 (Melton et al., Nucleic Acids Res. 12:7035-7056 (1984)). Restriction maps were generated as described by Maniatis et al., Molecular Cloning: A Laboratory Manual, (1982) and nucleotide sequences were determined using the method of Sanger et al., Proc. Natl. Acad. Sci., USA 74:5463-5467 (1977).

A computer search of nucleotide and protein sequences was conducted using the Protein Identification Resource Data (GenBank release 66 and Swiss-Prot-16). Gap penalties of −1 were assessed during sequence homology analysis for each nucleotide or amino acid in the sequence where a gap or deletion occurred.

RNA blot analysis

Poly(A)+ RNA was isolated as described (Maniatis et al., Molecular Cloning: A Laboratory Manual, (1982)). For Northern-blot analysis, 2 μg of poly(A)+ RNA was denatured with glyoxal, fractionated by electrophoresis through a 1.1% agarose gel and transferred to nitrocellulose (Thomas, Methods Enzymol. 100:255 (1983)). The pB123 CDNA insert used as probe was isolated, nick-translated (Rigby et al., J. Mol. Biol. 113:237–251 (1977)) and hybridized with the filters as described (Wahl et al., Proc. Natl. Acad. Sci., USA 76:3683–3687 (1979)). Hybridization at high stringency was with 50% (v/v) formamide, 4X SSC, 10% (W/V) Na dextran sulfate at 42° C. The filters were washed at 65° C. with 0.2X SSC, 0.1% SDS. RNA size was determined by comparison with 28S and 18S ribosomal RNA run on the same gels as standards. The same blot was also hybridized with CDNA clones containing a housekeeping MRNA of unknown identity revealing that all MRNA were intact and were similar in quantity of this expressed MRNA. For hybridization at low stringency the conditions are overnight incubation at 42° C. in a solution comprising: 20% formamide, 5XSSC (150 Mm NaCl, 15 Mm trisodium citrate), 50 mM sodium phosphate (pH 7.6), 5X Denhardts solution, 10% dextran sulfate, and 20 μg/ml denatured, sheared salmon sperm DNA.

Cells

Human blood was obtained by protocols approved by the Human Protection Committee of Dana-Farber Cancer Institute and mononuclear cells were isolated by Ficoll-Hypaque density gradient centrifugation. Mononuclear cells $10^6$/Mj) in complete media (RPMI-1640 supplemented with 15% fetal calfserum, antibiotics and glutamine) were stimulated with phytohemagglutinin-P (2 μg/ml; Difco, Detroit, Mich.), Con A (10 μg/ml, Miles Laboratories, Elkhart, Ind.), pokeweed mitogen (10 μ/ml, Gibco/BRL, Bethesda, Md.) or phorbol myristate 13-acetate (PMA, 10 μg/ml, Sigma, St. Louis, Mo.) as described (Tedder et al., J. Immunol. 144:532–540 (1990)). Lymphocytes were harvested at the indicated time points, washed once in complete media, and aliquoted for immediate immunofluorescence staining as described below.

COS cells were transfected with the pHB15 CDNA insert subcloned into a modified CDM8 vector (Aruffo et al., EMBO J. 6:3313 (1987); Tedder et al., J. Immunol. 143:712–717 (1989)) using the DEAE-dextran method as described (Aruffo et al., EMBO J. 6:3313 (1987)). Cell surface expression was examined after 48 hours by indirect immunofluorescence. Stable CDNA transfected cells were produced using the pHB15 CDNA cloned into the BamH I site of the retroviral vector pZipNeoSV(X) in the correct orientation (Cepko et al., Cell 37:1053–1062 (1984)). The murine pre-B cell line, 300.19, and the human erythroleukemia cell line, K562, were transfected with this vector by electroporation with subsequent selection of stable transfectants using G418 (Gibco/BRL). Cells expressing HB15 were further enriched by reacting the cells with monoclonal antibodies with the subsequent isolation of HB15+ cells by panning on anti-mouse Ig coated plates.

Cell lines were grown in RPMI 1640 medium containing 10% fetal calf serum and antibiotics. Cultures of all cell lines were split the day before analysis and were in logarithmic growth.

mAb production

Anti-HB15 mAb were generated as described (Tedder et al., J. Immunol. 144:532–540 (1990)) by the fusion of NS-1 myeloma cells with spleen cells from BALB/C mice that were repeatedly immunized with COS cells transfected with the HB15 CDNA. Each hybridoma was cloned twice and used to generate ascites fluid. The isotypes of the mAb were determined using a mouse monoclonal antibody isotyping kit from Amersham (Arlington Heights, Ill.).

Immunofluorescence analysis

Cells were kept at 4° C. and were examined immediately after isolation. Indirect immunofluorescence analysis of viable cells was carried out after washing the cells three times. The cells were then incubated for 20 min on ice with each mAb as ascites fluid diluted to the optimal concentration for immunostaining. Isotype-matched murine antibodies that were unreactive with human leukocytes were used as negative controls. After washing, the cells were treated for 20 min at 4° C. with fluorescein isothiocyanate-conjugated goat anti-mouse Ig antibodies (Southern Biotechnology Associates, Birmingham, Ala.). Single color immunofluorescence analysis was performed on an Epics Profile flow cytometer (Coulter Electronics, Hialeah, Fla.). Ten thousand cells were analyzed for each sample.

Immunoprecipitation analysis

Cells were washed twice, resuspended in saline and labeled by the iodogen method as described (Thompson et al., Biochem. 26:743–750 (1987)). After washing, the cells were lysed in 1 ml of buffer containing 1% (v/v), TRITON X-100 and protease inhibitors as described (Tedder et al., Proc. Natl. Acad. Sci., USA 85:208 (1988)). Immunoprecipitations were carried out using anti-HB15a mAb or mouse Ig (as a negative control) directly conjugated to AFFIGEL (BioRad, Richmond, Va.) at 2 mg ofmAb per ml of gel according to the manufacturer's instructions. Cell lysates were precleared twice for 2 hours using 50 μl (50% v/v) of murine Ig coated beads at 4° C. Cell lysates were precleared again overnight. Half of the precleared lysate was then incubated with 25 μl of anti-HB15a mab-coated beads or murine Ig-coated beads with constant rotation at 4° C. for 18 hours. Immunoprecipitates were washed and analyzed by SDS-PAGE as described (Tedder et al., Proc. Natl. Acad. Sci., USA 85:208 (1988)) with half of the sample run in the presence of 5% 2-mercaptoethanol (reducing conditions). $M_r$ were determined using pre-stained standard molecular weight markers (Gibco/BRL).

Immunohistochemistry

All tissues were stained applying a modification of the APAAP procedure as described by Cordell et al., J. Histochem. Cytochem. 31:219–229 (1984). Basically, the slides were first incubated with monoclonal antibody followed by an incubation step with rabbit anti-mouse (bridging) antibody. Subsequently, a monoclonal antibody against alkaline phosphatase pre-incubated with alkaline phosphatase was applied. In order to enhance the sensitivity of this procedure, the number of phosphatase molecules on the surface was increased by using one or two layers of bridging antibody and antiphosphatase antibody. Bound phosphatase molecules were visualized using new fuchsin as a substrate (Cordell et al., J. Histochem. Cytochem. 3-1:219–229 (1984)).

Use

The HB15 protein or immunospecific fragments thereof, or antibodies or other antagonists to HB15 function, can be used to diagnose or treat a variety of immunological disorders, diseases or syndromes. For such purposes, the soluble external domain would often be employed, typically but not necessarily, polymerized in a multivalent state using, e.g., dextran or polyamino acid carriers or fusion proteins of HB15 fragments and carrier molecules. Liposomes may alternatively be employed as the therapeutic vehicle, in which case the transmembrane domain and preferably at least some of the cytoplasmic domain will also be included.

For example, since Langerhans cells are the primary immunocompetent cell in the skin, playing a role in the presentation of antigen to T cells and the induction of contact hypersensitivity, and since HB15 is expressed by Langerhans cells and may be involved in antigen presentation, it is likely to be involved in the pathogenesis of human skin disease such as psoriasis, autoimmune disorders, organ transplant and AIDS.

Therefore, antagonists to HB15 function can provide important therapeutic agents for treatment of these diseases. Similarly, since HB15 may serve as an accessory molecule for lymphocyte activation, the HB15 antigen, fragments or domains thereof, may be used as agonists that would augment an immune response.

More specifically, the dendritic cell is a primary target of the human immunodeficiency virus, the causative agent of AIDS. It has recently been proposed that 80% of AIDS virus in vivo is produced by dendritic cells, particularly by Langerhans cells, circulating dendritic cells and interdigitating reticulum cells (Langhoff et al., Proc. Natl. Acad. Sci. USA 88:7998–8002 (1991)). Also, most infections occur through mucosal surfaces where it is thought that dendritic cells are first infected. Therefore, this reagent provides us with a critical tool for the potential prevention or treatment of AIDS or AIDS related disorders.

For monitoring certain clinical conditions, it may be advisable to quantitate the levels of endogenous soluble HB15 in a patient's blood serum. Based on the finding that several receptors are now known to be shed during various normal and pathological conditions, it is possible that HB15 is also lost from the cell surface by an enzymatic process. Also, quantitative detection can be useful in a method of identifying leukocytes with abnormal or decreased expression of HB15 for diagnosis and/or detection of leukocyte activation or altered leukocyte function. Additionally, the ability to quantitate the amount of receptor, or fragment thereof, produced during the manufacture of a recombinant therapeutic agent will be advantageous. Quantitation of HB15 levels can be carried out using a number of assay methods known to those of ordinary skill in the art, including an enzyme-linked immunoassay using the monoclonal antibodies that have been produced against HB15.

Similarly, in treating certain clinical conditions, it may be advisable to remove endogenous soluble HB15 or HB15+ cells from a patient's blood. This can be done with existing on-line and off-line techniques by employing immunoselection columns containing antibodies or other binding agents directed against the disclosed external domain of HB15.

There are at present no specific markers for non-follicular dendritic cells in humans. Use of HB15 monoclonal antibody to identify HB15+ cells now permits the isolation and purification of cells expressing this protein from a population of unrelated cells.

The HB15 mAb will also be useful for the evaluation and diagnosis of interdigitating cell sarcomas or other malignant cell types expressing this antigen. Therefore, HB15-based agents may be suitable for immunotherapy or immunoimaging.

In addition, assays for HB15 function can be used in further research on the physiological role of this receptor. For example, in preliminary experiments T cell proliferation in the mixed lymphocyte reaction, an assay for T cell activation, can be partially inhibited by the presence of anti-HB15 monoclonal antibodies. This functional assay suggests a role for the HB15 molecule on dendritic cells or monocytes in the initiation of T cell function.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

Deposits

The following hybridomas were deposited on Mar. 17, 1992, with the American Type Culture Collection (ATCC) under the terms of the Budapest Treaty.

| Identification | ATCC Designation |
| --- | --- |
| Anti-HB15a Hybridoma cell line, HB15a | HB 10987 |
| Anti-HB15b Hybridoma cell line, HB15b | HB 10988 |

Applicants' assignee, Dana-Farber Cancer Institute, Inc., represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

What is claimed is:

1. An isolated nucleic acid comprising a sequence encoding the extracellular domain of the HB15 protein described by SEQ ID NO: 2.

2. The nucleic acid of claim 1, comprising a sequence encoding the entire HB15 sequence shown in SEQ ID NO: 2.

3. The nucleic acid of claim 1, encoding the amino acid sequence corresponding to residues 1-113 of SEQ ID NO: 2.

4. The nucleic acid of claim 1, encoding the amino acid sequence of SEQ ID NO: 2.

5. An isolated nucleic acid comprising a sequence encoding a mammalian homolog of the HB15 protein, wherein said sequence encoding said homolog is capable of hybridizing under stringent conditions with a DNA probe comprising the coding sequence shown in SEQ ID NO: 1, and wherein said homolog has the tissue distribution observed for the human HB15 protein.

6. An isolated nucleic acid comprising that portion of the nucleic acid of claim 5 which encodes the extracellular domain of said homolog.

7. A recombinant vector comprising the nucleic acid of any one of claims 1-6.

8. The vector of claim 7, wherein said nucleic acid is operably associated with suitable control sequences.

9. A cultured cell transfected with the vector of claim 7.

10. A cultured cell transfected with the vector of claim 8.

11. The cell of claim 10, wherein said cell in the untransfected form does not express the protein encoded by said nucleic acid.

12. A method of expressing recombinant nucleic acid which comprises culturing the cell of claim 10 under conditions which allow for the expression of the nucleic acid with which it has been transfected.

13. An isolated nucleic acid comprising the coding sequence shown in SEQ ID NO: 1.

14. The nucleic acid of claim 13, comprising the entire sequence shown in SEQ ID NO: 1.

* * * * *

UNITED STATES PATENT AND TRADEMARK OFFICE
CERTIFICATE OF CORRECTION

PATENT NO. : 5,316,920

DATED : May 31, 1994

INVENTOR(S) : Thomas F. Tedder, et al.

It is certified that error appears in the above-indentified patent and that said Letters Patent is hereby corrected as shown below:

Column 1, line 66, "cDNAs loned" should read --cDNAs cloned--.

Column 2, line 2, "CDNA" should read --cDNA--.

Column 2, line 6, "MRNA" should read --mRNA--.

Column 3, line 12, "CDNA" should read --cDNA--.

Column 3, line 28, "100 bp. production" should read --100 bp. Assays for HB15 function, production--.

Column 3, line 36, "CDNA" should read --cDNA--.

Column 3, line 38, "transmission" should read --transmembrane--.

Column 3, line 42, "SEQ ID NO: 1" should read --SEQ ID NO: 2--.

Column 4, line 11, "HB15 expressed" should read --HB15, is expressed--.

Column 4, line 12, "Langerhans skin cells" should read --skin Langerhans cells--.

Column 4, line 15, "CDNA" should read --cDNA--.

Column 4, line 22, "CDNA" should read --cDNA--.

UNITED STATES PATENT AND TRADEMARK OFFICE
CERTIFICATE OF CORRECTION

PATENT NO. : 5,316,920

DATED : May 31, 1994

INVENTOR(S) : Thomas F. Tedder, et al.

Page 2 of 4

It is certified that error appears in the above-indentified patent and that said Letters Patent is hereby corrected as shown below:

Column 4, line 24, "CDNA" should read --cDNA--.

Column 4, line 31, "CDNA" should read --cDNA--.

Column 4, line 38, "(SEW" should read --(SEQ--.

Column 6, line 34, "CDNA" should read --cDNA--.

Column 6, line 37, 38, 40, 49, 64, 65, 68, "CDNA" should read ---cDNA--.

Column 6, line 45, 50, 52, 54, "MRNA" should read --mRNA--.

Column 7, line 4, 7, 11, 12, 41, 54, 58 reads "CDNA" should read --cDNA--.

Column 7, line 37, "MRNA" should read --mRNA--.

Column 8, line 42, "MRNA" should read --mRNA--.

Column 8, line 46, 47, 52, 56, 68 "CDNA" should read --cDNA--.

Column 9, line 16, "CDNA" should read --cDNA--.

UNITED STATES PATENT AND TRADEMARK OFFICE
CERTIFICATE OF CORRECTION

PATENT NO. : 5,316,920

DATED : May 31, 1994

INVENTOR(S) : Thomas F. Tedder, et al.

It is certified that error appears in the above-indentified patent and that said Letters Patent is hereby corrected as shown below:

Column 9, line 17, "PZIPNEDSV(X)" should read --PZIPNEOSV(X)--.

Column 9, line 33, "NAI.M-6" should read --NALM-6--.

Column 9, line 57, "cell-surf ace--" should read --cell-surface--.

Column 10, line 44, 45, 51, 52, 55 reads "CDNA" should read --cDNA--.

Column 11, line 9, 19, 48, 55, 56 "CDNA" should read --cDNA--.

Column 11, line 20, 21, 22 "MRNA" should read --mRNA--.

Column 11, line 24, 25 reads "Mm" should read --mM--.

Column 11, line 35, "$10_6$/Mj)" should read --$10^6$/ml)--.

Column 11, line 37, "calfserum" should read --calf serum--.

Column 12, line 9, "CDNA" should read --cDNA--.

Column 12, line 42, "ofmAb" should read --of mAb--.

Column 12, line 47, "mab-" should read --mAb- --.

Column 13, line 3, "3-1:219-229" should read --31:219-229--.

UNITED STATES PATENT AND TRADEMARK OFFICE
CERTIFICATE OF CORRECTION

PATENT NO. : 5,316,920

DATED : May 31, 1994

INVENTOR(S) : Thomas F. Tedder, et al.

It is certified that error appears in the above-indentified patent and that said Letters Patent is hereby corrected as shown below:

Column 13, line 58, "HB15levels" should read --HB15 levels--.

Signed and Sealed this

Seventh Day of May, 1996

*Attest:*

BRUCE LEHMAN

*Attesting Officer*   *Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 1762 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( i x ) FEATURE:
( A ) NAME/KEY: CDS
( B ) LOCATION: 11..625

( i x ) FEATURE:
( A ) NAME/KEY: matpeptide
( B ) LOCATION: 68..622

( x i ) SEQUENCE DESCRIPTION: SEQ ID NO:1:

```
GAATTCCGCC ATG TCG CGC GGC CTC CAG CTT CTG CTC CTG AGC TGC GCC              49
           Met Ser Arg Gly Leu Gln Leu Leu Leu Leu Ser Cys Ala
           -19         -15                     -10

TAC AGC CTG GCT CCC GCG ACG CCG GAG GTG AAG GTG GCT TGC TCC GAA             97
Tyr Ser Leu Ala Pro Ala Thr Pro Glu Val Lys Val Ala Cys Ser Glu
    -5              1               5                       10

GAT GTG GAC TTG CCC TGC ACC GCC CCC TGG GAT CCG CAG GTT CCC TAC            145
Asp Val Asp Leu Pro Cys Thr Ala Pro Trp Asp Pro Gln Val Pro Tyr
                15              20                  25

ACG GTC TCC TGG GTC AAG TTA TTG GAG GGT GGT GAA GAG AGG ATG GAG            193
Thr Val Ser Trp Val Lys Leu Leu Glu Gly Gly Glu Glu Arg Met Glu
            30                  35                  40

ACA CCC CAG GAA GAC CAC CTC AGG GGA CAG CAC TAT CAT CAG AAG GGG            241
Thr Pro Gln Glu Asp His Leu Arg Gly Gln His Tyr His Gln Lys Gly
        45                  50                  55

CAA AAT GGT TCT TTC GAC GCC CCC AAT GAA AGG CCC TAT TCC CTG AAG            289
Gln Asn Gly Ser Phe Asp Ala Pro Asn Glu Arg Pro Tyr Ser Leu Lys
    60                  65                  70

ATC CGA AAC ACT ACC AGC TGC AAC TCG GGG ACA TAC AGG TGC ACT CTG            337
Ile Arg Asn Thr Thr Ser Cys Asn Ser Gly Thr Tyr Arg Cys Thr Leu
75                  80                  85                  90

CAG GAC CCG GAT GGG CAG AGA AAC CTA AGT GGC AAG GTG ATC TTG AGA            385
Gln Asp Pro Asp Gly Gln Arg Asn Leu Ser Gly Lys Val Ile Leu Arg
                95                  100                 105

GTG ACA GGA TGC CCT GCA CAG CGT AAA GAA GAG ACT TTT AAG AAA TAC            433
Val Thr Gly Cys Pro Ala Gln Arg Lys Glu Glu Thr Phe Lys Lys Tyr
            110                 115                 120

AGA GCG GAG ATT GTC CTG CTG CTG GCT CTG GTT ATT TTC TAC TTA ACA            481
Arg Ala Glu Ile Val Leu Leu Leu Ala Leu Val Ile Phe Tyr Leu Thr
        125                 130                 135

CTC ATC ATT TTC ACT TGT AAG TTT GCA CGG CTA CAG AGT ATC TTC CCA            529
Leu Ile Ile Phe Thr Cys Lys Phe Ala Arg Leu Gln Ser Ile Phe Pro
    140                 145                 150

GAT TTT TCT AAA GCT GGC ATG GAA CGA GCT TTT CTC CCA GTT ACC TCC            577
Asp Phe Ser Lys Ala Gly Met Glu Arg Ala Phe Leu Pro Val Thr Ser
155                 160                 165                 170

CCA AAT AAG CAT TTA GGG CTA GTG ACT CCT CAC AAG ACA GAA CTG GTA            625
Pro Asn Lys His Leu Gly Leu Val Thr Pro His Lys Thr Glu Leu Val
                175                 180                 185
```

| | | | | |
|---|---|---|---|---|
| TGAGCAGGAT | TTCTGCAGGT | TCTTCTTCCT | GAAGCTGAGG | CTCAGGGGTG | TGCCTGTCTG | 685 |
| TTACACTGGA | GGAGAGAAGA | ATGAGCCTAC | GCTGAAGATG | GCATCCTGTG | AAGTCCTTCA | 745 |
| CCTCACTGAA | AACATCTGGA | AGGGGATCCC | ACCCCATTTT | CTGTGGGCAG | GCCTCGAAAA | 805 |
| CCATCACATG | ACCACATAGC | ATGAGGCCAC | TGCTGCTTCT | CCATGGCCAC | CTTTTCAGCG | 865 |
| ATGTATGCAG | CTATCTGGTC | AACCTCCTGG | ACATTTTTC | AGTCATATAA | AAGCTATGGT | 925 |
| GAGATGCAGC | TGGAAAAGGG | TCTTGGGAAA | TATGAATGCC | CCCAGCTGGC | CCGTGACAGA | 985 |
| CTCCTGAGGA | CAGCTGTCCT | CTTCTGCATC | TTGGGGACAT | CTCTTTGAAT | TTTCTGTGTT | 1045 |
| TTGCTGTACC | AGCCCAGATG | TTTTACGTCT | GGGAGAAATT | GACAGATCAA | GCTGTGAGAC | 1105 |
| AGTGGGAAAT | ATTTAGCAAA | TAATTTCCTG | GTGTGAAGGT | CCTGCTATTA | CTAAGGAGTA | 1165 |
| ATCTGTGTAC | AAAGAAATAA | CAAGTCGATG | AACTATTCCC | CAGCAGGGTC | TTTTCATCTG | 1225 |
| GGAAAGACAT | CCATAAAGAA | GCAATAAAGA | AGAGTGCCAC | ATTTATTTT | ATATCTATAT | 1285 |
| GTACTTGTCA | AAGAAGGTTT | GTGTTTTCT | GCTTTTGAAA | TCTGTATCTG | TAGTGAGATA | 1345 |
| GCATTGTGAA | CTGACAGGCA | GCCTGGACAT | AGAGAGGGAG | AAGAAGTCAG | AGAGGGTGAC | 1405 |
| AAGATAGAGA | GCTATTTAAT | GGCCGGCTGG | AAATGCTGGG | CTGACGGTGC | AGTCTGGGTG | 1465 |
| CTCGTCCACT | TGTCCCACTA | TCTGGGTGCA | TGATCTTGAG | CAAGTTCCTT | CTGGTGTCTG | 1525 |
| CTTTCTCCAT | TGTAAACCAC | AAGGCTGTTG | CATGGGCTAA | TGAAGATCAT | ATACGTGAAA | 1585 |
| ATTCTTTGAA | AACATATAAA | GCACTATACA | GATTCGAAAC | TCCATTGAGT | CATTATCCTT | 1645 |
| GCTATGATGA | TGGTGTTTTG | GGGATGAGAG | GGTGCTATCC | ATTTCTCATG | TTTTCCATTG | 1705 |
| TTTGAAACAA | AGAAGGTTAC | CAAGAAGCCT | TTCCTGTAGC | CTTCTGTAGG | AATTCCA | 1762 |

( 2 ) INFORMATION FOR SEQ ID NO:2:

( i ) SEQUENCE CHARACTERISTICS:
        ( A ) LENGTH: 205 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ser  Arg  Gly  Leu  Gln  Leu  Leu  Leu  Ser  Cys  Ala  Tyr  Ser  Leu
-19            -15                 -10                      -5

Ala  Pro  Ala  Thr  Pro  Glu  Val  Lys  Val  Ala  Cys  Ser  Glu  Asp  Val  Asp
               1                 5                      10

Leu  Pro  Cys  Thr  Ala  Pro  Trp  Asp  Pro  Gln  Val  Pro  Tyr  Thr  Val  Ser
     15                 20                      25

Trp  Val  Lys  Leu  Leu  Glu  Gly  Gly  Glu  Glu  Arg  Met  Glu  Thr  Pro  Gln
30                      35                      40                           45

Glu  Asp  His  Leu  Arg  Gly  Gln  His  Tyr  His  Gln  Lys  Gly  Gln  Asn  Gly
                    50                      55                      60

Ser  Phe  Asp  Ala  Pro  Asn  Glu  Arg  Pro  Tyr  Ser  Leu  Lys  Ile  Arg  Asn
               65                      70                      75

Thr  Thr  Ser  Cys  Asn  Ser  Gly  Thr  Tyr  Arg  Cys  Thr  Leu  Gln  Asp  Pro
          80                      85                      90

Asp  Gly  Gln  Arg  Asn  Leu  Ser  Gly  Lys  Val  Ile  Leu  Arg  Val  Thr  Gly
     95                      100                     105

Cys  Pro  Ala  Gln  Arg  Lys  Glu  Glu  Thr  Phe  Lys  Lys  Tyr  Arg  Ala  Glu
110                     115                     120                          125

Ile  Val  Leu  Leu  Leu  Ala  Leu  Val  Ile  Phe  Tyr  Leu  Thr  Leu  Ile  Ile
                    130                     135                     140

Phe  Thr  Cys  Lys  Phe  Ala  Arg  Leu  Gln  Ser  Ile  Phe  Pro  Asp  Phe  Ser
```

```
                    145                         150                              155
Lys  Ala  Gly  Met  Glu  Arg  Ala  Phe  Leu  Pro  Val  Thr  Ser  Pro  Asn  Lys
               160                    165                    170

His  Leu  Gly  Leu  Val  Thr  Pro  His  Lys  Thr  Glu  Leu  Val
          175                    180                185
```